(12) United States Patent
Fu et al.

(10) Patent No.: US 7,934,501 B2
(45) Date of Patent: May 3, 2011

(54) SWIVEL ELBOW FOR A PATIENT INTERFACE

(75) Inventors: Timothy Tsun-Fai Fu, Carlingford (AU); Jim Saada, Kellyville (AU)

(73) Assignee: ResMed Limited, Bella Vista (AU)

( * ) Notice: Subject to any disclaimer, the term of this patent is extended or adjusted under 35 U.S.C. 154(b) by 982 days.

(21) Appl. No.: 11/630,261

(22) PCT Filed: Jul. 25, 2005

(86) PCT No.: PCT/AU2005/001091
§ 371 (c)(1),
(2), (4) Date: Dec. 20, 2006

(87) PCT Pub. No.: WO2006/007668
PCT Pub. Date: Jan. 26, 2006

(65) Prior Publication Data
US 2008/0047561 A1  Feb. 28, 2008

Related U.S. Application Data

(60) Provisional application No. 60/590,338, filed on Jul. 23, 2004.

(51) Int. Cl.
*A62B 18/02* (2006.01)
(52) U.S. Cl. .......... 128/206.21; 128/205.25; 128/207.13
(58) Field of Classification Search ............. 128/206.21, 128/206.27, 207.11, 207.12, 207.17, 205.27, 128/207.16, 205.25, 207.13
See application file for complete search history.

(56) References Cited

U.S. PATENT DOCUMENTS

| | | | |
|---|---|---|---|
| 1,081,745 A | 12/1913 | Johnston | |
| 2,313,999 A | 3/1943 | Kreiselman | |
| 4,266,540 A | 5/1981 | Panzik et al. | |
| 4,488,548 A * | 12/1984 | Agdanowski | 128/204.25 |
| 4,655,213 A | 4/1987 | Rapoport et al. | |
| 4,676,241 A | 6/1987 | Webb et al. | |
| 4,713,844 A | 12/1987 | Westgate | |
| 4,794,921 A | 1/1989 | Lindkvist | |
| 4,944,310 A | 7/1990 | Sullivan | |
| 5,243,971 A | 9/1993 | Sullivan et al. | |
| 5,245,995 A | 9/1993 | Sullivan et al. | |
| 5,349,949 A | 9/1994 | Schegerin | |
| 5,438,981 A | 8/1995 | Starr et al. | |
| 5,441,046 A | 8/1995 | Starr et al. | |
| RE35,339 E | 10/1996 | Rapoport | |

(Continued)

FOREIGN PATENT DOCUMENTS

DE  29715718 U1  12/1997

(Continued)

OTHER PUBLICATIONS

Supplementary Search Report issued in EP Appln. No. 05763002.2, mailed on Oct. 23, 2009.

(Continued)

*Primary Examiner* — Kristen C Matter
(74) *Attorney, Agent, or Firm* — Nixon & Vanderhye P.C.

(57) ABSTRACT

A swivel elbow includes a conduit pathway separated from a vent airflow pathway for conducting respective gas flow streams in use. The swivel elbow further includes baffle structure that separates the respective gas flow streams so that they do not interfere with each other within an interior (e.g., breathing chamber) of a mask to which the elbow is connected in use.

53 Claims, 15 Drawing Sheets

U.S. PATENT DOCUMENTS

| | | |
|---|---|---|
| 5,560,354 A | 10/1996 | Berthon-Jones et al. |
| 5,657,752 A | 8/1997 | Landis et al. |
| 5,662,101 A | 9/1997 | Ogden et al. |
| 5,694,922 A | 12/1997 | Palmer |
| 5,704,345 A | 1/1998 | Berthon-Jones et al. |
| 5,746,201 A | 5/1998 | Kidd |
| 5,918,598 A | 7/1999 | Belfer et al. |
| 5,921,239 A | 7/1999 | McCall et al. |
| 5,937,851 A | 8/1999 | Serowski et al. |
| 5,947,121 A | 9/1999 | Marshall |
| 6,112,745 A | 9/2000 | Lang |
| 6,112,746 A | 9/2000 | Kwok et al. |
| 6,119,693 A | 9/2000 | Kwok et al. |
| 6,119,694 A | 9/2000 | Correa et al. |
| 6,192,886 B1 * | 2/2001 | Rudolph .................. 128/207.13 |
| 6,347,631 B1 | 2/2002 | Hansen et al. |
| 6,412,487 B1 | 7/2002 | Gunaratnam et al. |
| 6,412,488 B1 * | 7/2002 | Barnett et al. ........... 128/206.26 |
| 6,418,928 B1 | 7/2002 | Bordewick et al. |
| 6,422,238 B1 | 7/2002 | Lithgow |
| 6,435,181 B1 | 8/2002 | Jones et al. |
| 6,467,483 B1 | 10/2002 | Kopacko et al. |
| 6,491,034 B1 | 12/2002 | Gunaratnam |
| 6,505,623 B1 | 1/2003 | Hansen |
| 6,530,373 B1 | 3/2003 | Patron et al. |
| 6,536,435 B1 | 3/2003 | Fecteau et al. |
| 6,561,190 B1 | 5/2003 | Kwok |
| 6,561,191 B1 | 5/2003 | Kwok |
| 6,581,594 B1 | 6/2003 | Drew et al. |
| 6,662,803 B2 | 12/2003 | Gradon et al. |
| D485,905 S | 1/2004 | Moore et al. |
| 6,675,796 B2 | 1/2004 | McDonald |
| 6,679,265 B2 | 1/2004 | Strickland et al. |
| D486,225 S | 2/2004 | Guney et al. |
| 6,691,707 B1 | 2/2004 | Gunaratnam et al. |
| 6,763,828 B2 | 7/2004 | Arnott |
| 6,823,869 B2 | 11/2004 | Raje et al. |
| 6,851,425 B2 | 2/2005 | Jaffre et al. |
| 6,851,427 B1 | 2/2005 | Nashed |
| 6,907,882 B2 | 6/2005 | Ging et al. |
| 7,011,090 B2 | 3/2006 | Drew et al. |
| 7,316,230 B2 | 1/2008 | Drew et al. |
| 7,487,772 B2 | 2/2009 | Ging et al. |
| 7,597,100 B2 | 10/2009 | Ging et al. |
| 2002/0029780 A1 | 3/2002 | Frater et al. |
| 2003/0005931 A1 | 1/2003 | Jaffre |
| 2003/0196656 A1 | 10/2003 | Moore et al. |
| 2003/0196657 A1 | 10/2003 | Ging |
| 2003/0196658 A1 | 10/2003 | Ging et al. |
| 2004/0112385 A1 | 6/2004 | Drew et al. |
| 2006/0102185 A1 | 5/2006 | Drew et al. |

FOREIGN PATENT DOCUMENTS

| | | |
|---|---|---|
| DE | 29723101 U1 | 7/1998 |
| EP | 1258266 A1 | 11/2002 |
| EP | 1314446 A2 | 5/2003 |
| EP | 1 356 844 A2 | 10/2003 |
| EP | 1057494 B1 | 11/2004 |
| EP | 1027905 B1 | 6/2005 |
| GB | 799225 | 8/1958 |
| GB | 2379886 A | 3/2003 |
| JP | 2000-233024 | 8/2000 |
| JP | 2000-279520 | 10/2000 |
| WO | WO 98/12965 | 4/1998 |
| WO | WO 98/34665 | 8/1998 |
| WO | WO 99/61088 | 12/1999 |
| WO | 2000/0078381 A1 | 12/2000 |
| WO | WO 00/78381 | 12/2000 |
| WO | WO 00/78384 | 12/2000 |
| WO | WO 01/97893 | 12/2001 |
| WO | WO 02/20078 | 3/2002 |
| WO | WO 02/096342 | 12/2002 |
| WO | 2004/0022147 A1 | 3/2004 |
| WO | WO 2004/022147 | 3/2004 |

OTHER PUBLICATIONS

International Search Report for PCT/AU2005/001091 mailed Sep. 19, 2005.
U.S. Appl. No. 60/377,254, dated May 2002, Moore et al.
U.S. Appl. No. 60/397,195, dated Jul. 2002, Moore et al.
U.S. Appl. No. 60/402,509, dated Aug. 2002, Moore et al.
PCT International Search Report dated Oct. 15, 2003.
Supplementary European Search Report for copending European Application No. 03793492, mailed Jun. 15, 2010.
Japanese Office Action and English Translation for copending Japanese Application No. 2004-569778, issued Mar. 25, 2009, 6 pages.

* cited by examiner

SWIVEL ELBOW FOR A PATIENT INTERFACE

CROSS-REFERENCES TO RELATED APPLICATIONS

This application is the U.S. national phase of international application PCT/AU2005/001091 filed 25 Jul. 2005 which designated the U.S. and claims the benefit of U.S. Provisional Application No. 60/590,338 filed 23 Jul. 2004, each incorporated herein by reference in its entirety.

STATEMENT REGARDING FEDERALLY SPONSORED RESEARCH OR DEVELOPMENT

None.

BACKGROUND OF THE INVENTION

1. Field of the Invention

The invention relates to a swivel elbow for use with patient interfaces used in the treatment of sleep disordered breathing.

2. Background of the Invention

Since the invention by Colin Sullivan of the use of nasal Continuous Positive Airway Pressure (nasal CPAP) to treat "snoring sickness" (see U.S. Pat. No. 4,944,310) there have a number of advances directed towards improving the noise and comfort of therapy. In nasal CPAP therapy, a supply of air at positive pressure is delivered to the entrance of a patient's airways via an air delivery conduit and some form of patient interface, such as a mask. The early masks were custom made for each patient and glued on each night. A typical mask comprises:

(i) a frame which defines a nose-receiving mask cavity;
(ii) a seal-forming face-contacting cushion which in use is positioned between the frame and the patient's face; and
(iii) a vent to atmosphere which amongst other things allows exhaled $CO_2$ to vent to atmosphere, thus reducing $CO_2$ rebreathing.

It is generally desirable for the treatment system (including the source of pressurised air and the patient interface) to be as quiet as possible so as not to disturb sleep.

The supply of air at positive pressure may be provided by a blower, sometimes referred to as a flow generator. Such devices typically include an electric motor and impeller housed in a volute. Spinning the motor (and thus the impeller) generates a flow of air. When the flow is attached to an air circuit, a pressure is created due to the impedance of the circuit. Spinning the motor faster generates a supply of air at higher pressure, but also more noise. As a fluid such as air flows through a pipe or conduit it loses pressure. Bends and curves in the pipe affect the amount of pressure loss. See Perry's Chemical Engineers Handbook 6th Edition, McGrawHill, 1984, Section 5, Fluid and Particle mechanics. The greater the pressure drop in each component (i.e. the higher the impedance) of the air circuit (for example along the air delivery conduit) the harder the blower must work in order to provide sufficient pressure in the patient interface. The harder the blower has to work, the greater noise it will generate. Thus generally it is important to design components in the air path to have a low impedance.

A further reason for minimising the impedance of components in the air path is to minimise pressure swings as the pressure fluctuates within the mask due to the patient breathing. A higher entry impedance at the mask will lead to a higher pressure difference between inspiration and expiration, which may lead to patient discomfort and additional cyclic noise.

The process of air venting from the mask creates noise. Since patients must wear their mask all night while sleeping, there is a need for the vent to be quiet. Some quiet vents are described in U.S. Pat. No. 6,561,190 (Kwok et al.) and U.S. Pat. No. 6,561,191 (Kwok et al.). The contents of these two patents are hereby expressly incorporated by cross-reference.

Whilst in some mask designs—such as the ResMed MIRAGE® mask—the air delivery conduit is fixed in position in relation to the frame, other masks—such as the ResMed ULTRA MIRAGE® mask—include a swivel elbow. The swivel elbow enables the air delivery conduit to rotate with respect to the mask. This enables a patient to place the air delivery conduit in a preferred position such as over the head or on the left or right sides. Absent a swivel, inadvertent movement of the air delivery conduit can disrupt the seal and thus therapy.

In designing hard parts for patient interfaces, such as a mask frame and elbow constructed from polycarbonate or similar materials, regard must be had to how the part will be moulded. For ease of manufacture, the tool from which a component is manufactured generally has two parts that form the shape of the component. Once the component has been formed, the tool is opened by withdrawing one part along a 'line of draw' that is of constant radius (including a straight line). Parts must be designed within the constraints of what is manufacturable.

Some swivel elbows, such as the one used in ResMed's ULTRA MIRAGE® mask, incorporate a vent. See U.S. Pat. No. 6,691,707 (Gunaratnam et al.). Incorporating a vent in a swivel elbow can allow the patient some control over the direction in which air is vented. Thus the vented air may be directed away from the patient or anyone sleeping close by. Incorporation of a vent in an elbow can simplify moulding of the mask frame.

Vent flow rate, and hence vent $CO_2$ flow rate is a function of the pressure differential between the mask interior and ambient pressure. The higher the differential, the higher the flow rate. With a fixed vent, whether adequate $CO_2$ washout occurs is defined by what happens at the lowest operating mask pressure, typically 4 $cmH_2O$. The flow rate is also a function of vent geometry.

In some prior art vents incorporated in elbows air entering the elbow from a blower can short-circuit the mask and pass straight out the vent.

Another known swivel elbow which includes a vent is described in International Patent Application PCT/AU2003/001162 (published as WO 2004/022147) Drew et al. the contents of which are hereby expressly incorporated by cross-reference. This elbow includes a baffle in the elbow as described in the '1162 PCT application. A commercial version of this elbow is found in ResMed's ACTIVA mask system.

A potential problem with including a baffle in the elbow is that while it may assist with $CO_2$ washout, it may impede flow from the blower. Increased impedance from a baffle may require a blower to work harder to generate enough pressure and thus result in increased noise. A poorly designed baffle and corresponding vent may be unnecessarily noisy. A possible way of avoiding increased impedance is to make the elbow larger overall, however this is undesirable for other reasons such as aesthetics.

BRIEF SUMMARY OF THE INVENTION

In accordance with a first aspect of the invention there is provided a compact low impedance swivel elbow incorporating a quiet vent which provides adequate $CO_2$ washout.

In accordance with another aspect of the invention there is provided a swivel elbow including a baffle which divides an interior of the elbow into a conduit pathway and a vent pathway, the baffle being positioned adjacent an interior wall of the conduit pathway.

In accordance with another aspect of the invention, there is provided a swivel elbow including a baffle which defines a part annular vent pathway.

In accordance with another aspect of the invention, there is provided a swivel elbow having separate conduit and vent airflow pathways for conducting respective airflow streams in use and further including baffle structure which separates said respective airflow streams so that they do not interfere with each other within an interior of a mask to which the elbow is connected in use.

Another aspect of the invention is a swivel elbow which incorporates a pressure port.

In accordance with another aspect of the invention there is provided a noise reducing structure for separating two airflow streams that pass close to one another.

In accordance with still another aspect of the invention, there is provided a vent elbow comprising a generally L-shaped main body having a frame engaging portion and a base portion, a conduit pathway to deliver an incoming gas flow stream from the base portion towards the frame engaging portion, a vent pathway to allow an outgoing gas flow stream to flow from the frame engaging portion towards a vent formed in the main body, a cylindrical portion extending from the frame engaging portion, and a baffle provided to the main body to separate and at least partly define the conduit pathway and the vent pathway, wherein the baffle is part annular or part cylindrical and has an axis that is concentric with an axis of the cylindrical portion.

These and other aspects of the invention are described in and/or apparent from the following description of exemplary embodiments.

DETAILED DESCRIPTION OF THE INVENTION

Figure 1:
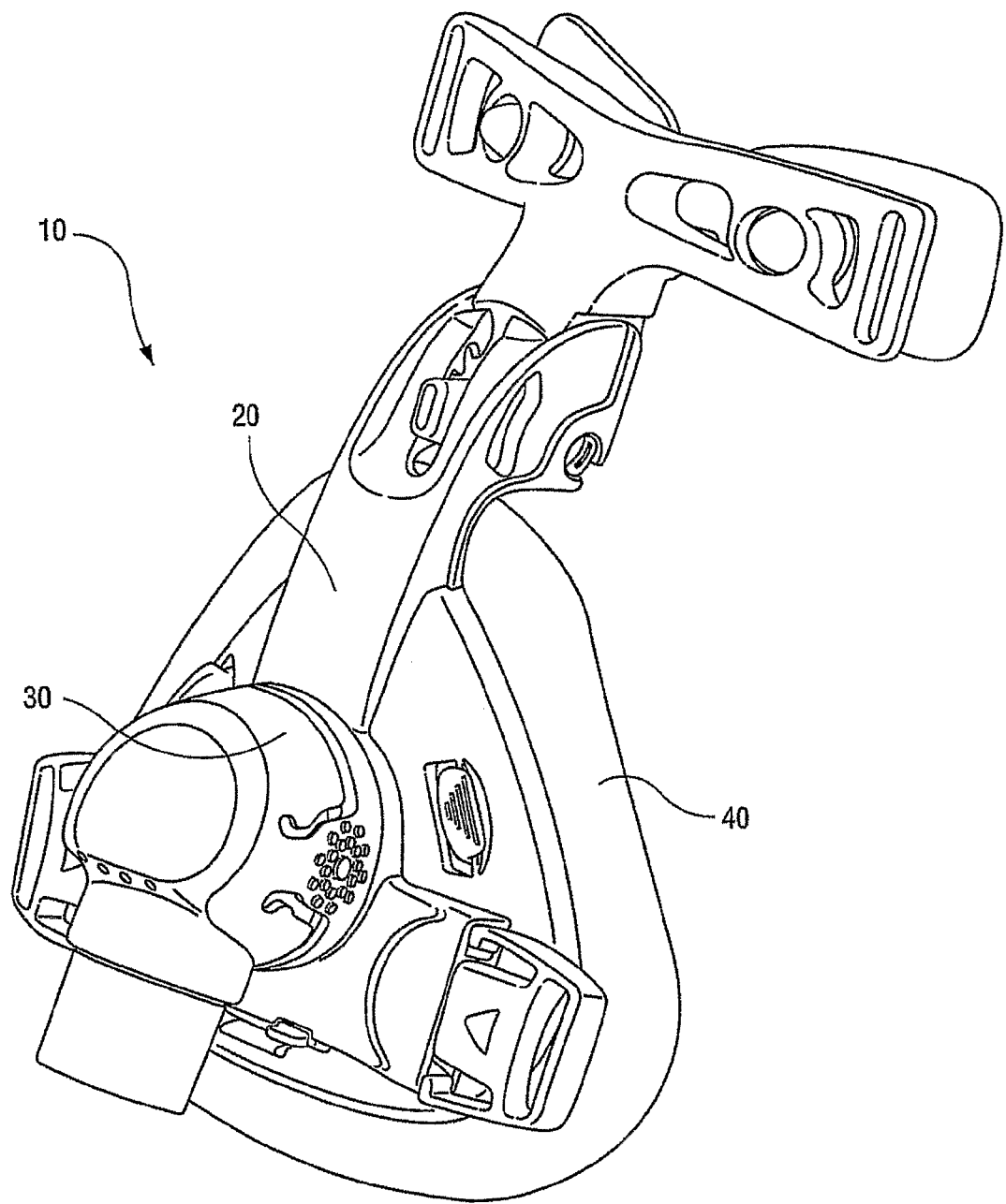
FIG. 1 shows a perspective view of prior art ACTIVA mask assembly (Reproduced from U.S. Design D486,226)
Figure 2:
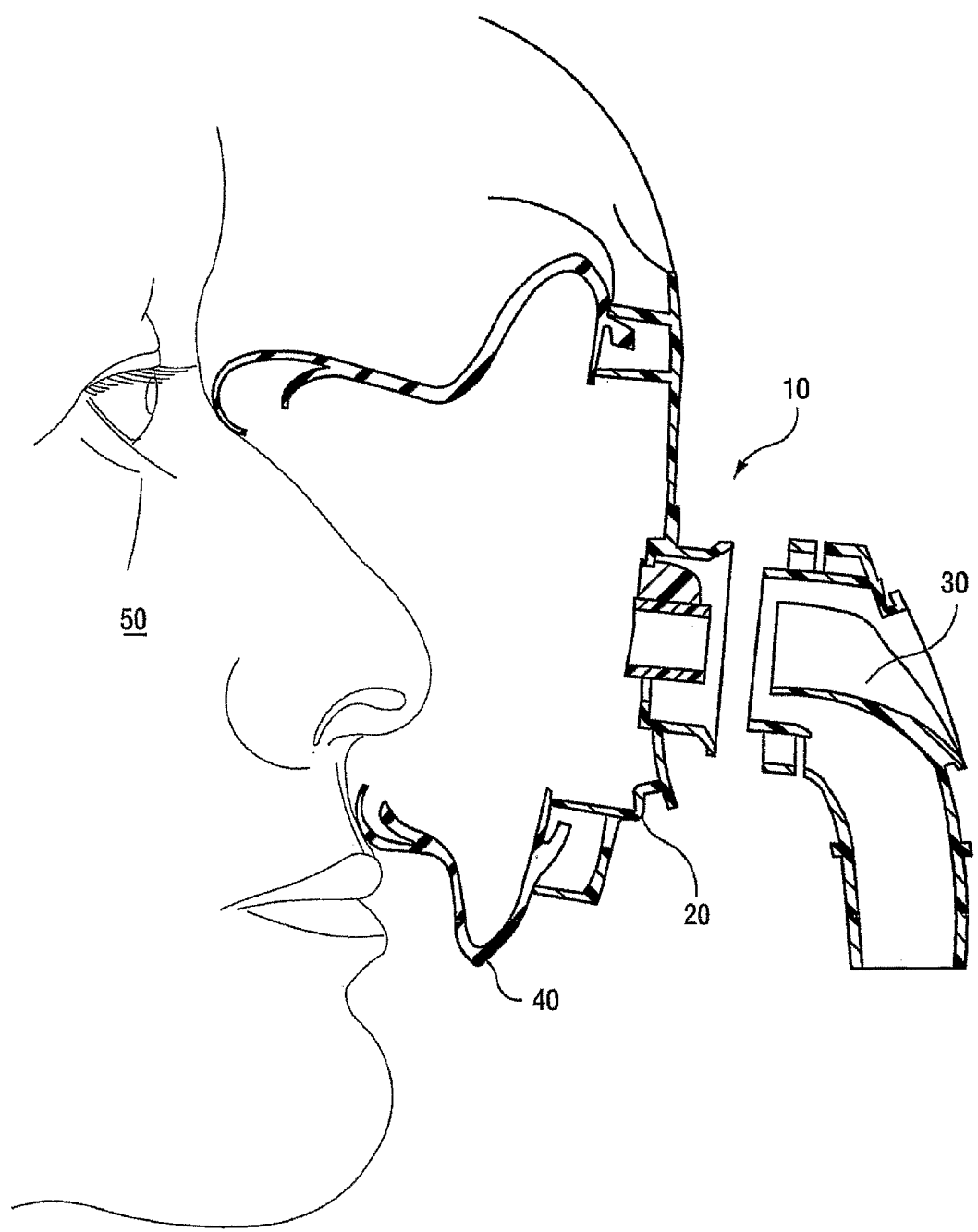
FIG. 2 shows a side view of a patient wearing prior art mask assembly including a cushion, frame and swivel elbow. The mask assembly is shown in cross-section. (Reproduced from PCT/AU2003/001162)
Figure 3:
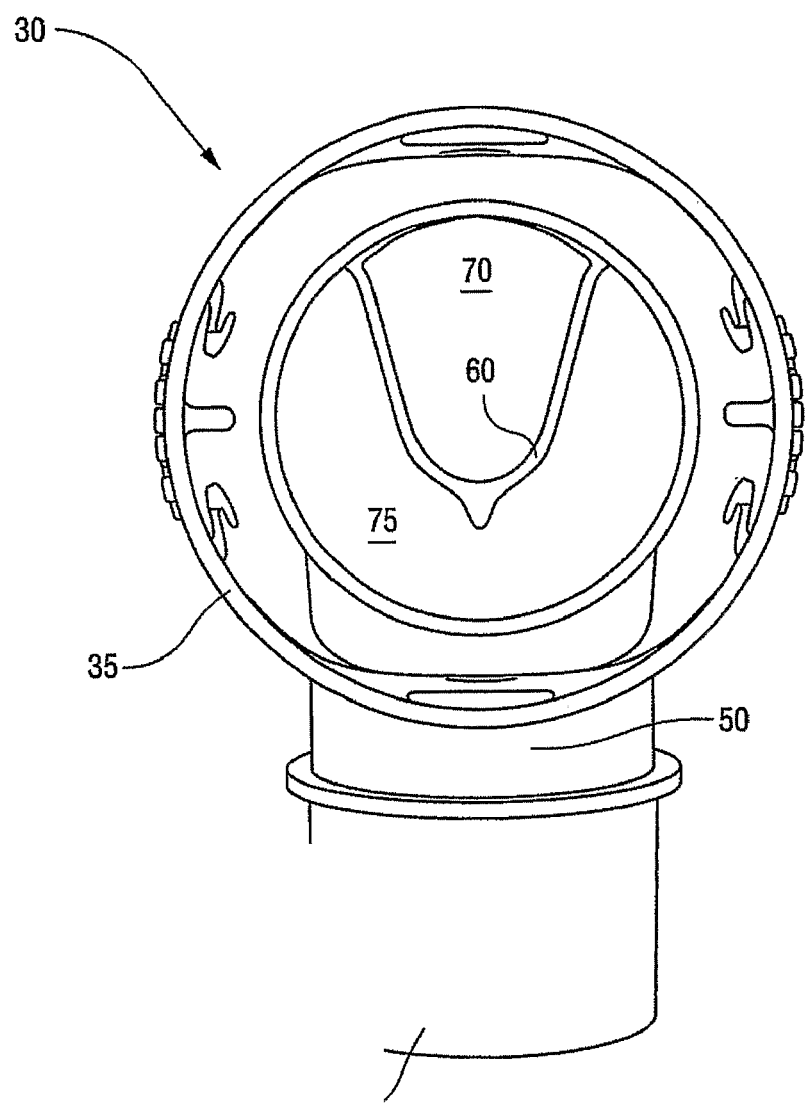
FIG. 3 shows a rear view of prior art ACTIVA swivel elbow including a baffle.

It is noted that two embodiments are shown in the figures. The first embodiment has 100-series numbers, the second embodiment 200-series number. Corresponding features have corresponding numbers, hence the baffle is numbered 160 in the first embodiment and 260 in the second embodiment. Where in the following description reference is made to a feature for one embodiment, generally the same description applies to the second embodiment.

In a preferred form the invention is applied to a swivel elbow. Preferably the swivel elbow is removably replaceable on a mask frame.

A swivel elbow 130 in accordance with an embodiment of the invention has a main body that is generally L-shaped. It comprises a frame-engaging portion 135 and base portion 150. The base portion 150 includes a generally cylindrical section 155 over which in use an end of an air delivery conduit (not shown) may be friction fit (or otherwise engaged). The frame engaging portion 135 includes a series of slots 137 adapted to engage with a frame (not shown). The frame engaging portion also includes generally cylindrical portion 180. See FIG. 5 to FIG. 9a-9e.

Within the swivel elbow 130 two fluid pathways are defined by baffle 160. A conduit pathway 175 allows flow between the air delivery conduit and the mask cavity. A vent pathway 170 allows flow between the mask cavity and atmosphere. In one form the vent pathway 170 forms part of an annulus. In a preferred form the baffle 160 is part-cylindrical, having an axis 161 (See FIG. 7). It is arranged to be generally concentric with cylindrical portion 180, that is their respective axes are generally co-linear. The ends of the baffle 160 subtend an angle of up to 180° with respect to its axis. It is noted that extending the baffle so that it subtended an angle greater than 180° might cause it to impinge on the conduit pathway 175. Hence preferably the angle is 180°. In a preferred form, the baffle 160 is spaced from generally cylindrical portion 180 by four spacers 165 and vent pathway 170. In other forms, fewer or more spacers may be used. By increasing the angle which the baffle 160 subtends, it is possible to decrease the height of the spacers 165. In this way the baffle 160 is positioned generally close to cylindrical portion 180 and does not impinge significantly on air flowing along conduit pathway 175. This arrangement leaves the cross-section of the incoming conduit pathway 175 as close to a circle as possible which provides minimum impedance for a given elbow size. Thus the impedance of the conduit pathway 175 is not significantly increased by the presence of the baffle 160.

As best seen in the cross-sections shown in FIGS. 9a-9e and 10 the vent pathway 270 generally tapers from a wider inlet 272 positioned adjacent the mask interior to a narrow outlet 274 positioned adjacent atmosphere. In a preferred form the vent pathway 270 has a first approximately constant cross-section region 273 along approximately ⅔ of its length from the inlet 272. A second narrower approximately constant cross-section 276 lies adjacent narrow outlet 274. In between the first and second approximately constant cross-section regions 273, 276 there is a tapering region 277. See FIG. 10.

Figure 4:
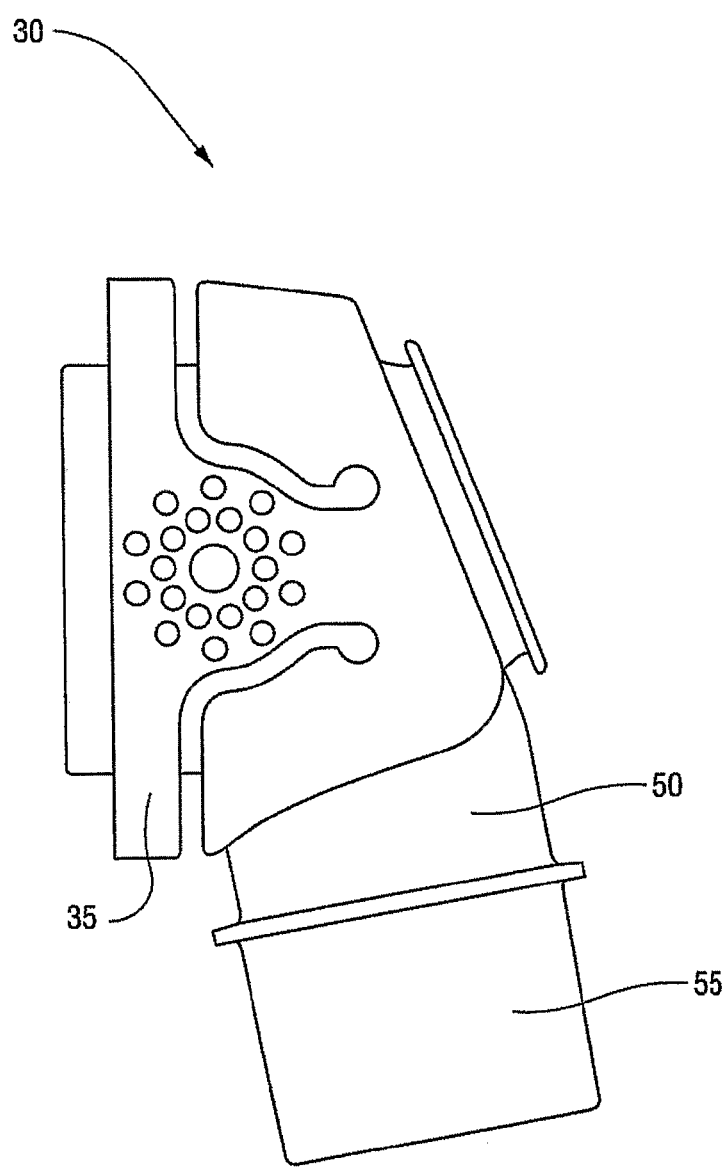
FIG. 4 shows a side view of prior art ACTIVA swivel elbow.

In a preferred form a lip portion 162, 262 the baffle 160, 260 extends more than approximately 1.5 mm, preferably 1.8 mm into the mask cavity. Compare FIG. 4 and FIG. 5. See also FIG. 9a and FIG. 10. Extending the baffle reduces noise and improves $CO_2$ washout. An extension of less than 1.5 mm may not provide significant improvement in noise and CO2 washout. Extending the baffle beyond 2.5 mm may increase the risk that it will interfere with the tip of a patient's nose in use. Hence an extension of 1.8 mm is preferred.

In some prior devices air from the conduit pathway 275 can flow directly across the inlet 272 of the vent pathway 270 causing an audible tone. The extension of the baffle reduces or prevents air from so passing directly over the inlet 272 and thus reduces or eliminates the tone.

Extension of the baffle into the mask cavity directs incoming airstreams or gas streams (via conduit pathway 175) and outgoing airstreams (via vent pathway 170) so that they do not interfere with each other. Prior art baffles tend to give rise to the situation where there are two narrow and relative fast airstreams moving parallel to each other but in opposite directions. The extended baffle causes the airstreams to remain separate until the inlet air has slowed down and the two airstreams have diverged. Hence there will be much less interference between the streams and the resultant turbulence and increase in noise is avoided.

Figure 9A:
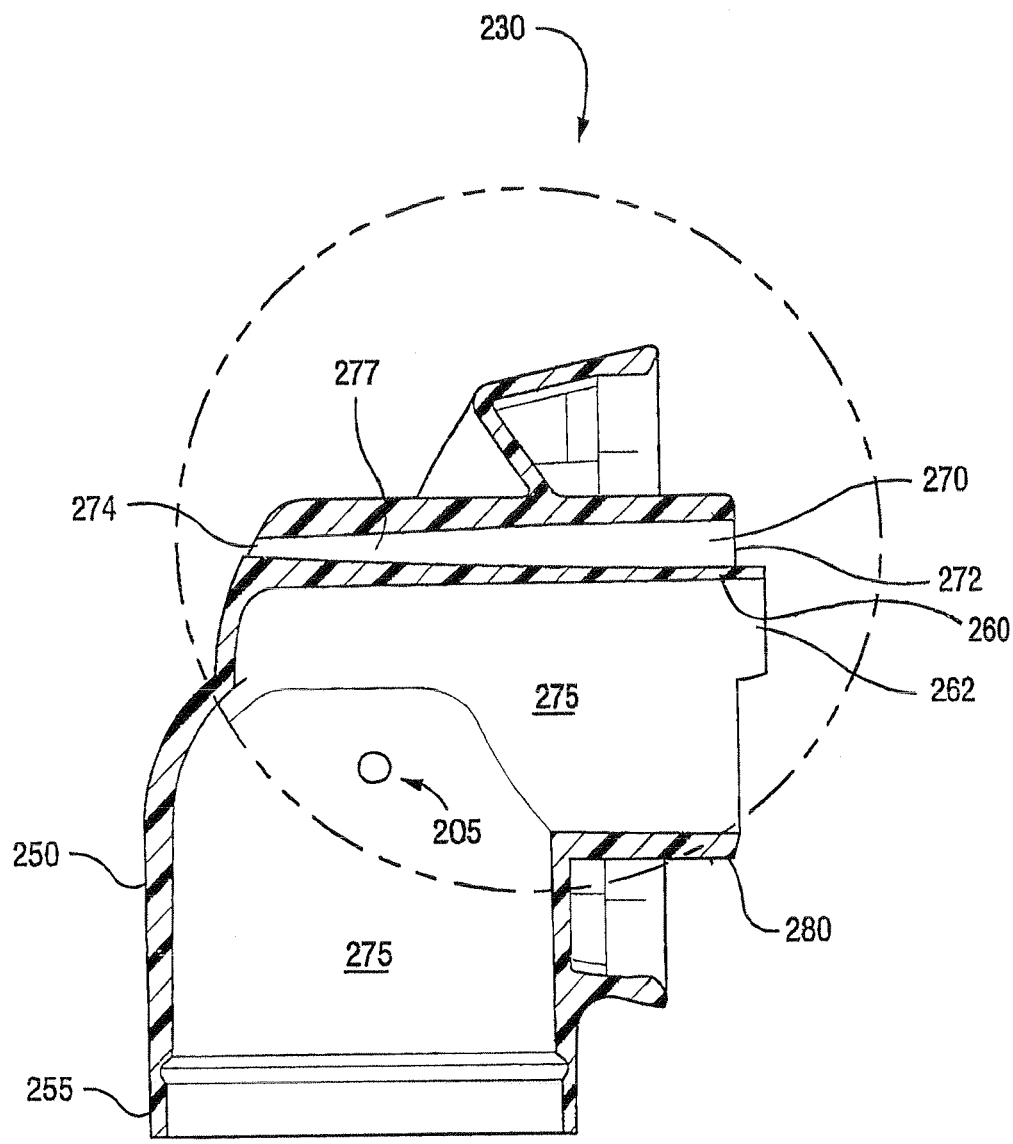
FIGS. 9a-9e show cross-sections of different variants taken along line 9a-9a of the elbow of FIG. 8. The circle shown in FIGS. 9a-9e is the approximate region a detail of which is shown in FIG. 10.
Figure 9B:
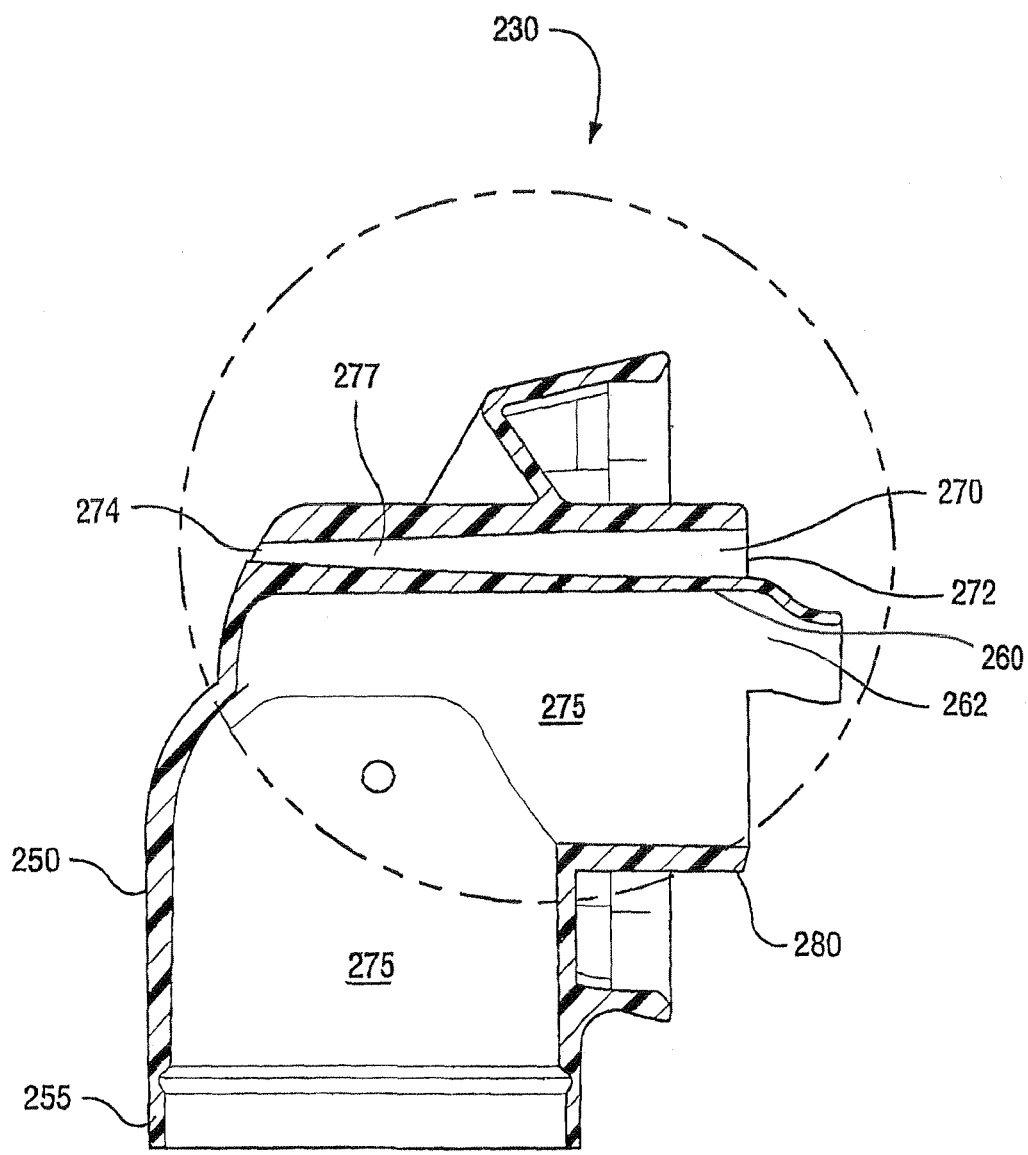
Figure 9C:
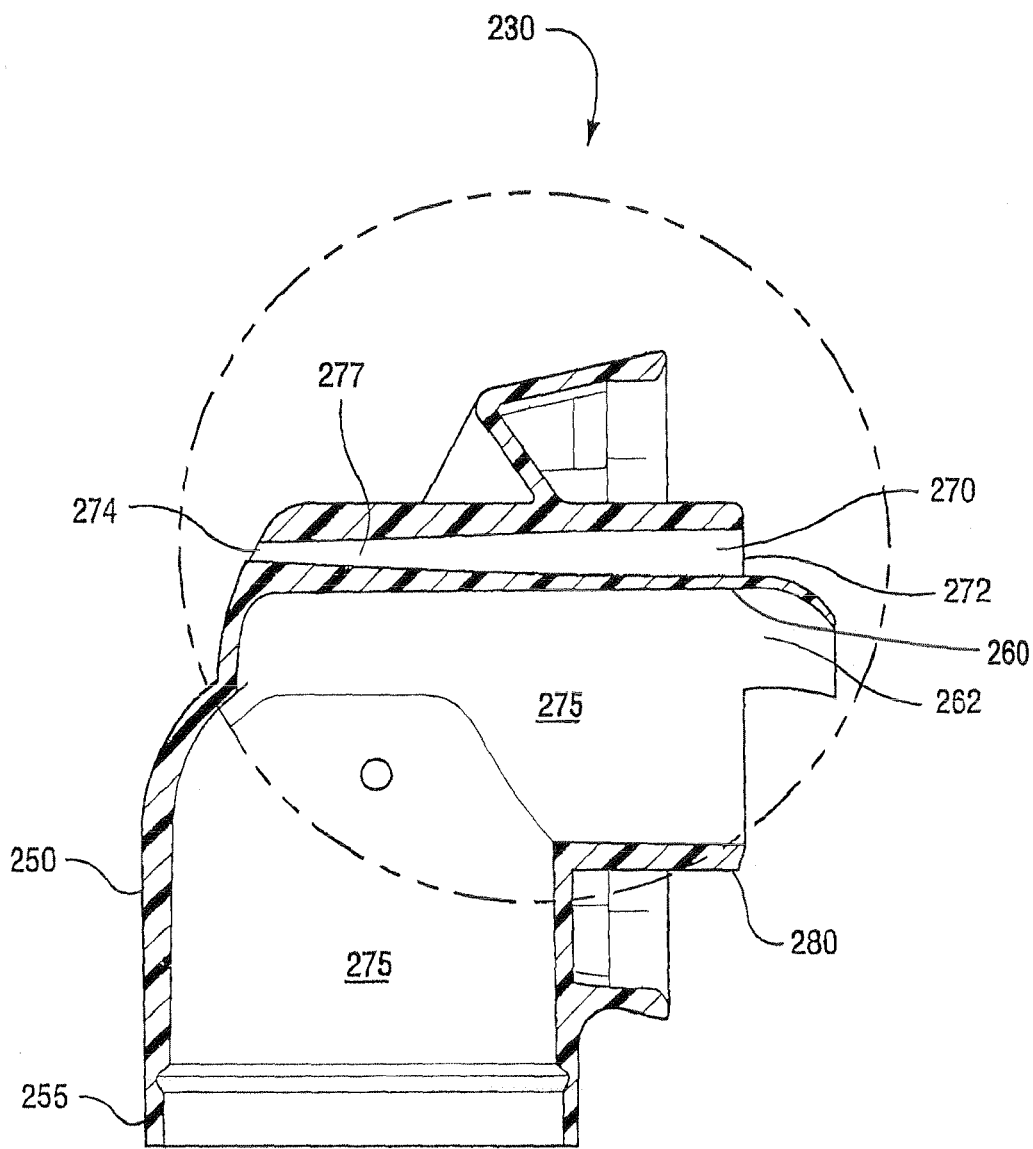
Figure 9D:
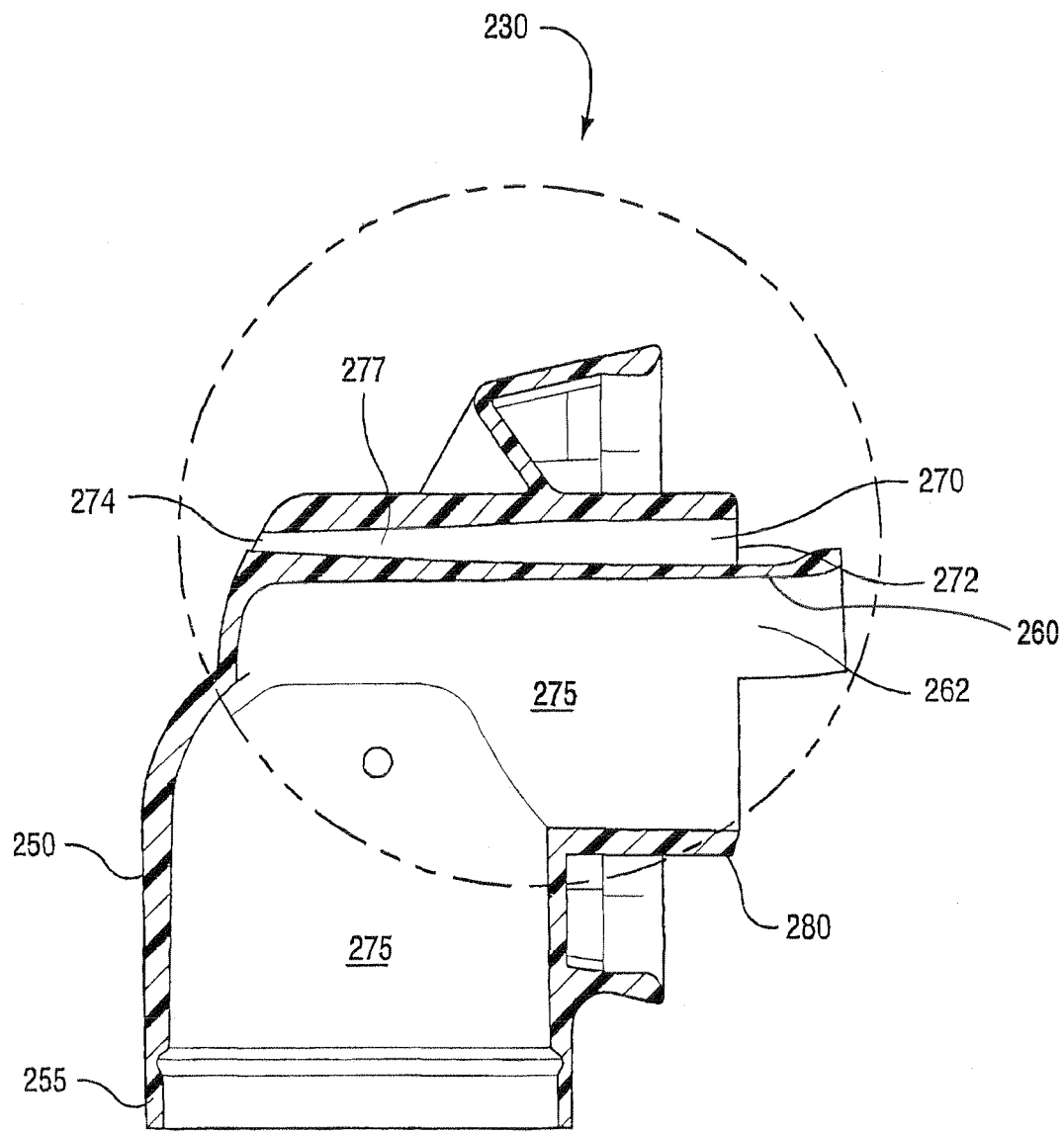
Figure 9E:
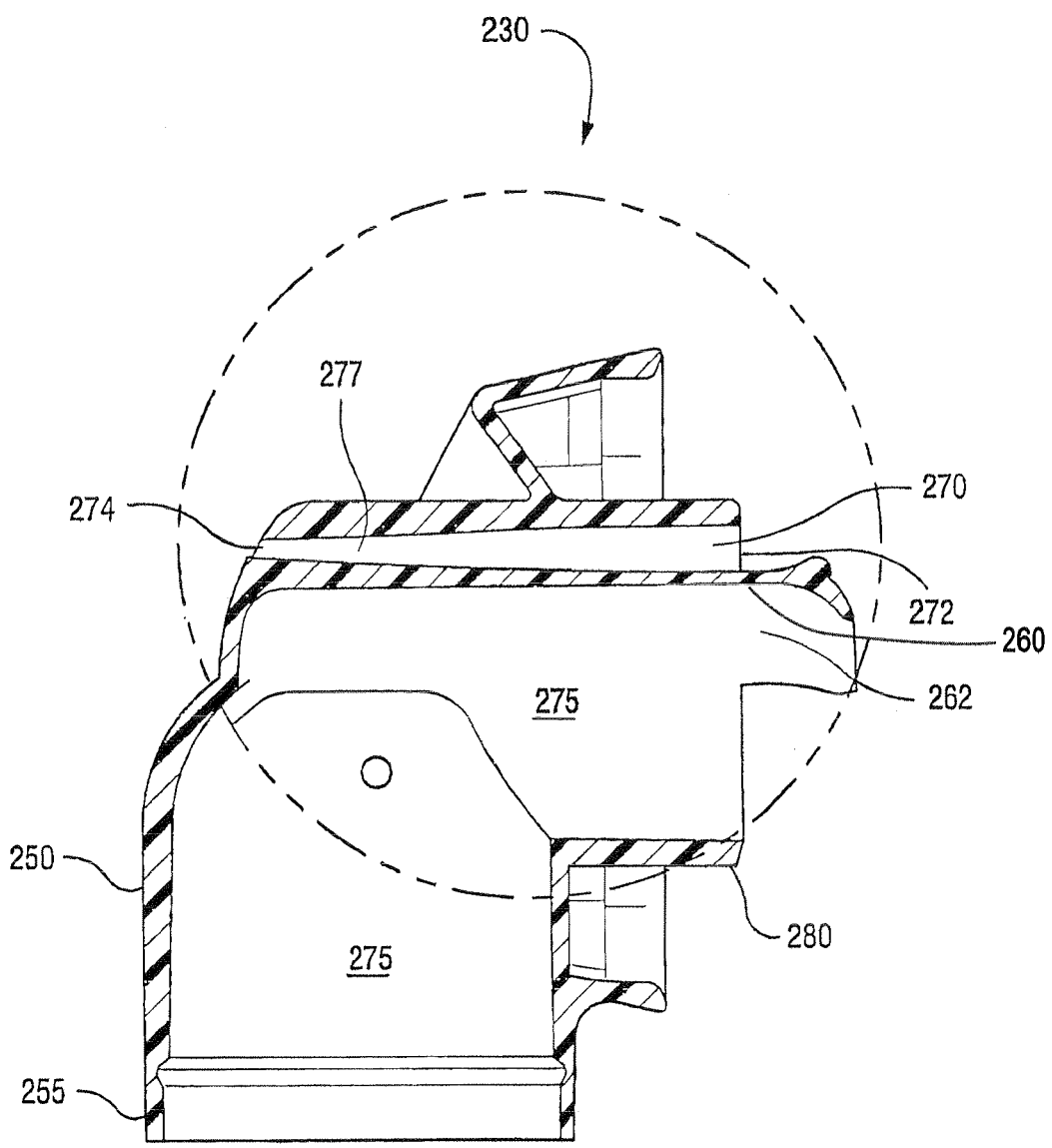
Figure 10:
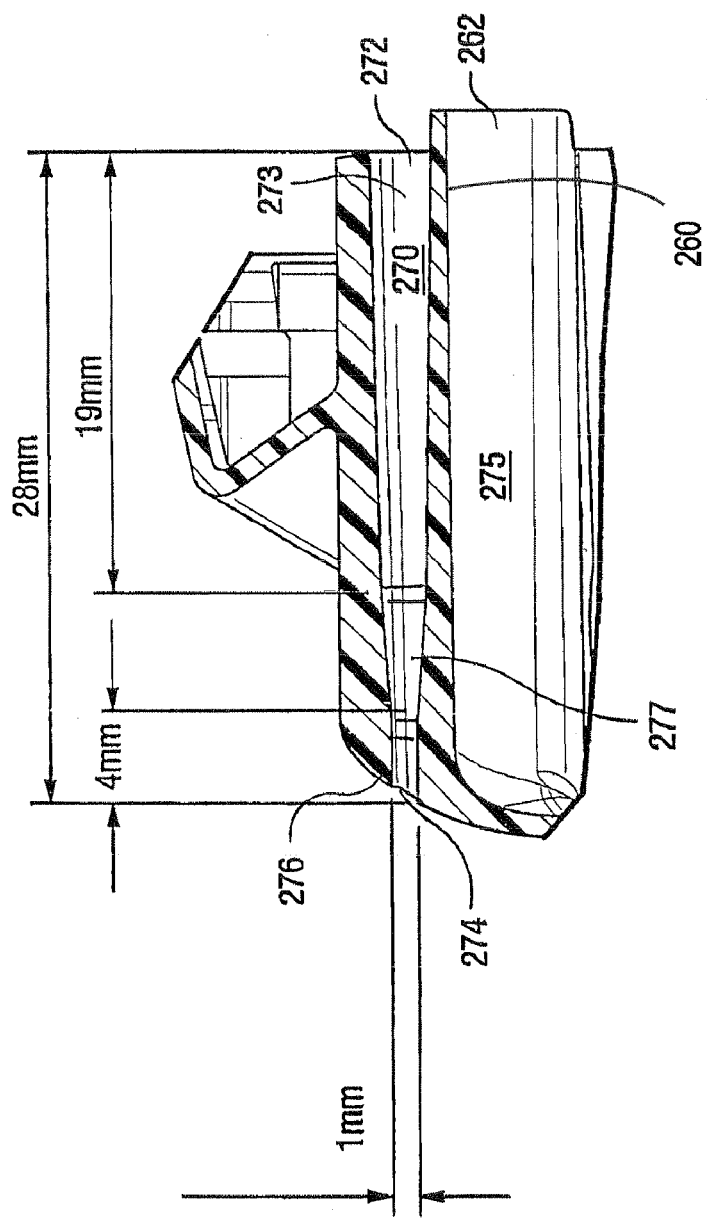
FIG. 10 shows detail from FIG. 9a with and exemplary approximate dimensions shown in millimeters.

There are other ways of separating the incoming and outgoing airstreams. Shaping the baffle within the mask cavity as shown in FIGS. 9b-9e may help to reduce interference between the incoming and outgoing airstreams. These variations have been developed to help separate the two airpaths and to minimise the shear and turbulence between the streams. The baffles shown in FIGS. 9b and 9c have portions that are shaped to direct the incoming air away from the outgoing airstream and vent. As well as reducing noise, this assists in allowing the fresh inlet air to reach the patient. The baffle shown in FIG. 9d has a portion that is shaped to smoothly guide the exhaled air into the vent pathway. FIG. 9e combines the advantages of 9c and 9d. The aforesaid portions of the baffle may be upwardly-and/or downwardly curved or bent to orient the gas stream(s) in the desired location.

A swivel elbow as shown in FIGS. 5-7 and 8, 9a and 10 is relatively simple to mould since all features are in the line of draw. The variations shown in FIG. 9b-9e may be more complicated to mould.

Figure 5:
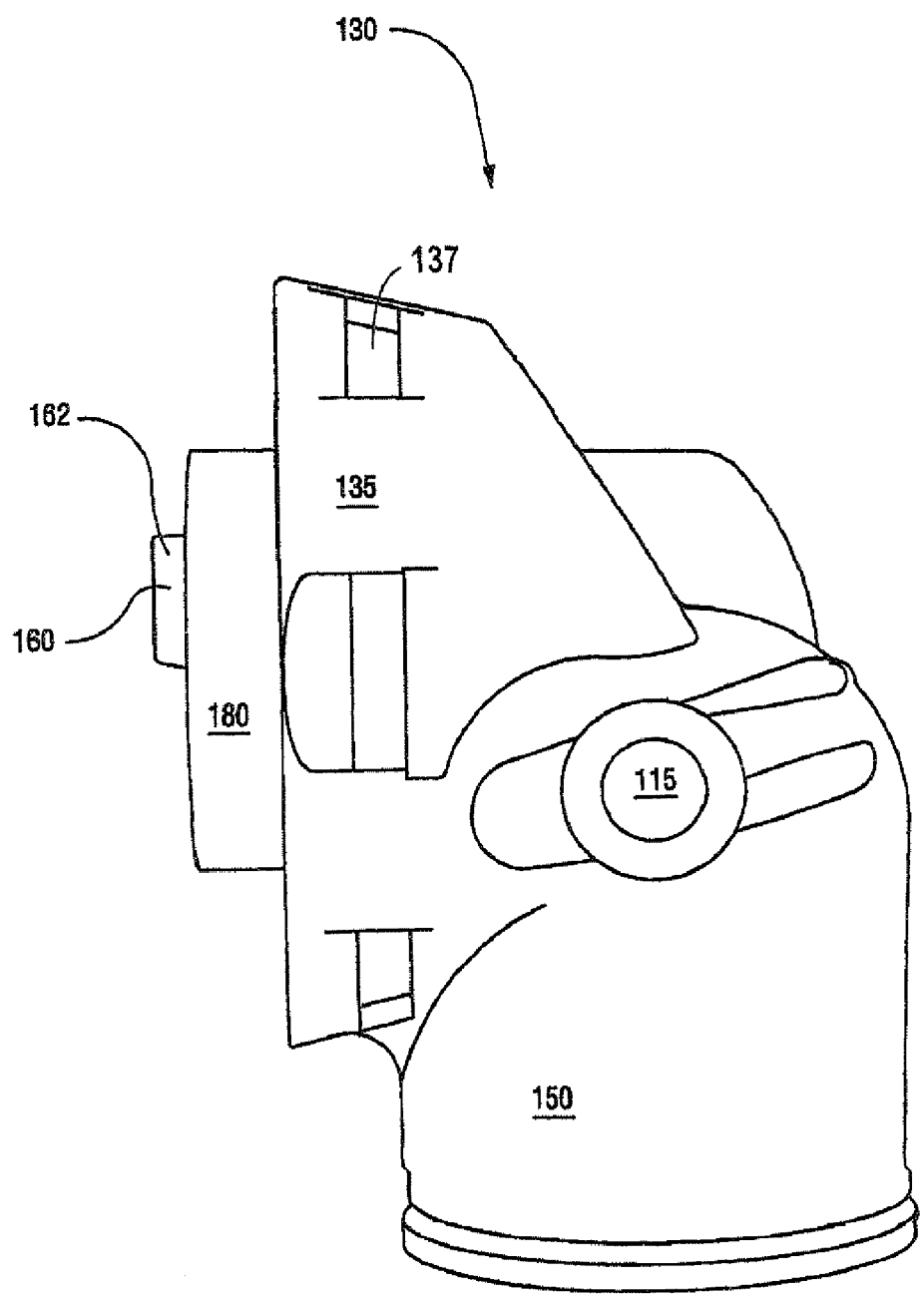
FIG. 5 shows a side view of a swivel elbow in accordance with a first embodiment of the invention.
Figure 6:
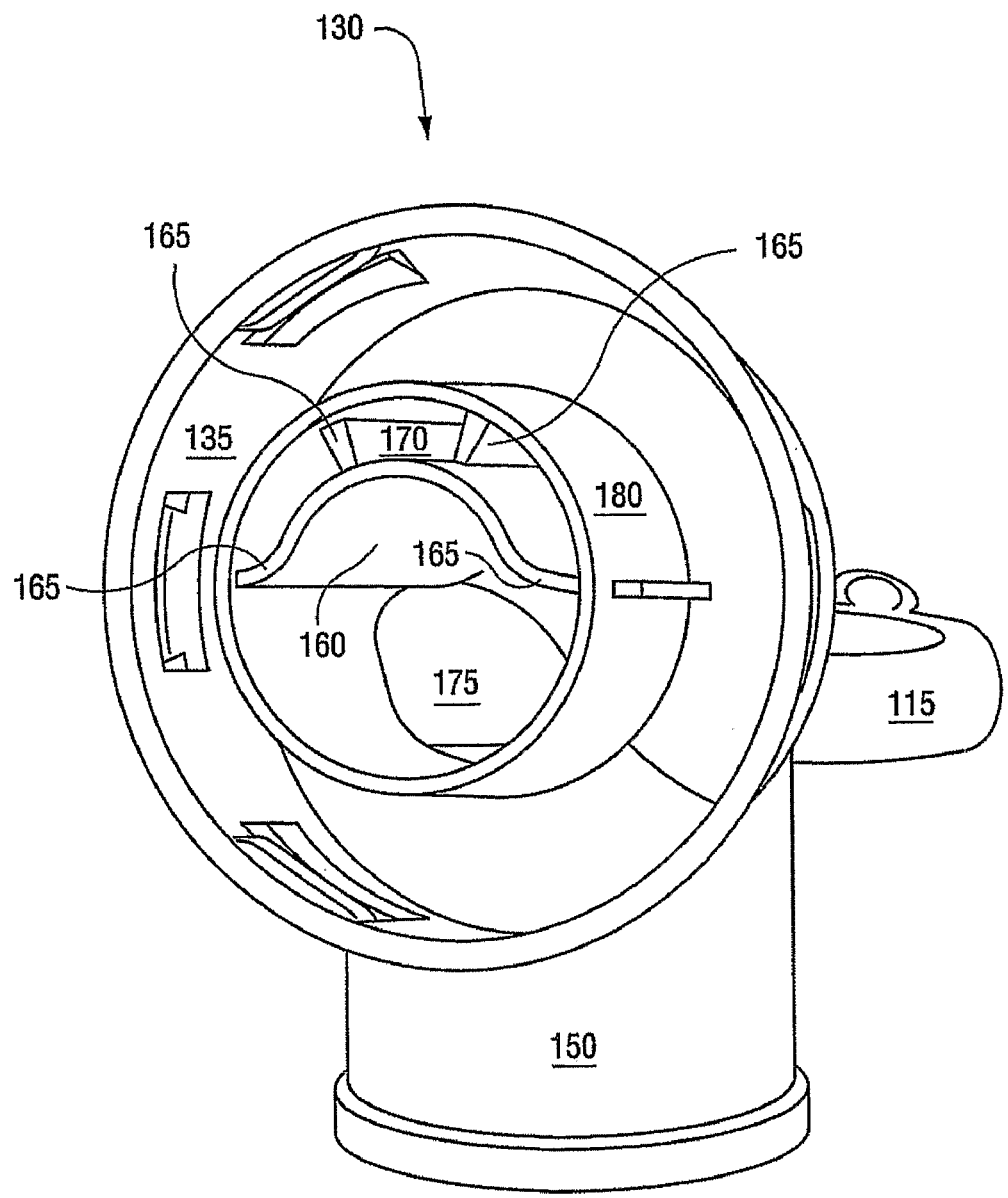
FIG. 6 shows a rear perspective view of the elbow of FIG. 5.
Figure 7:
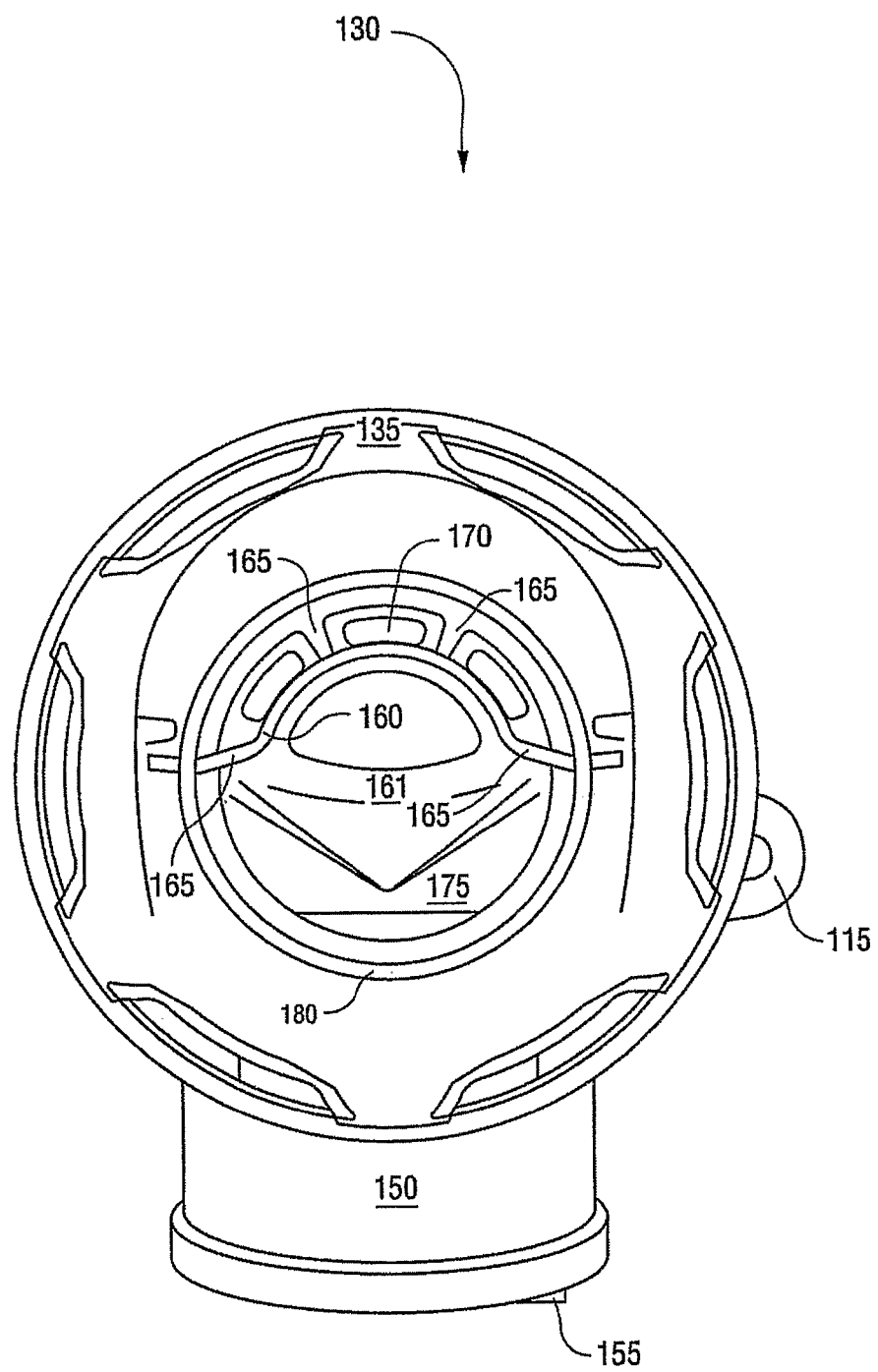
FIG. 7 shows a rear view of the elbow of FIG. 5.
Figure 8:
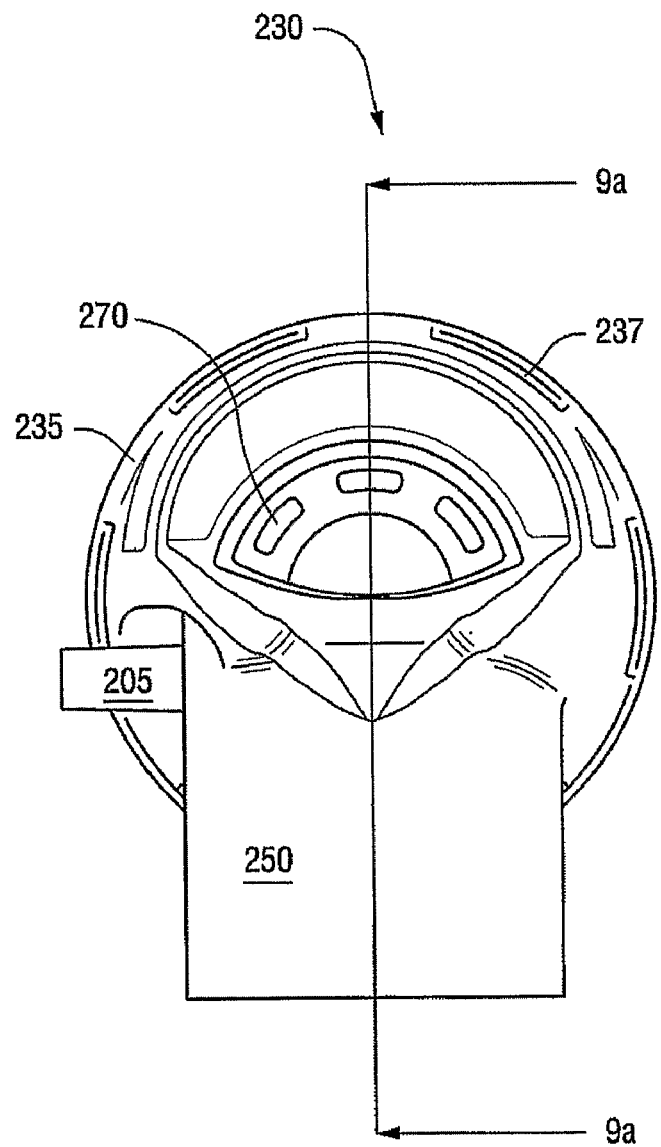
FIG. 8 shows a front view of an elbow in accordance with a second embodiment of the invention. In this and following figures, thicker lines show edges while thinner lines are tangent lines on surfaces.
Figure 11:
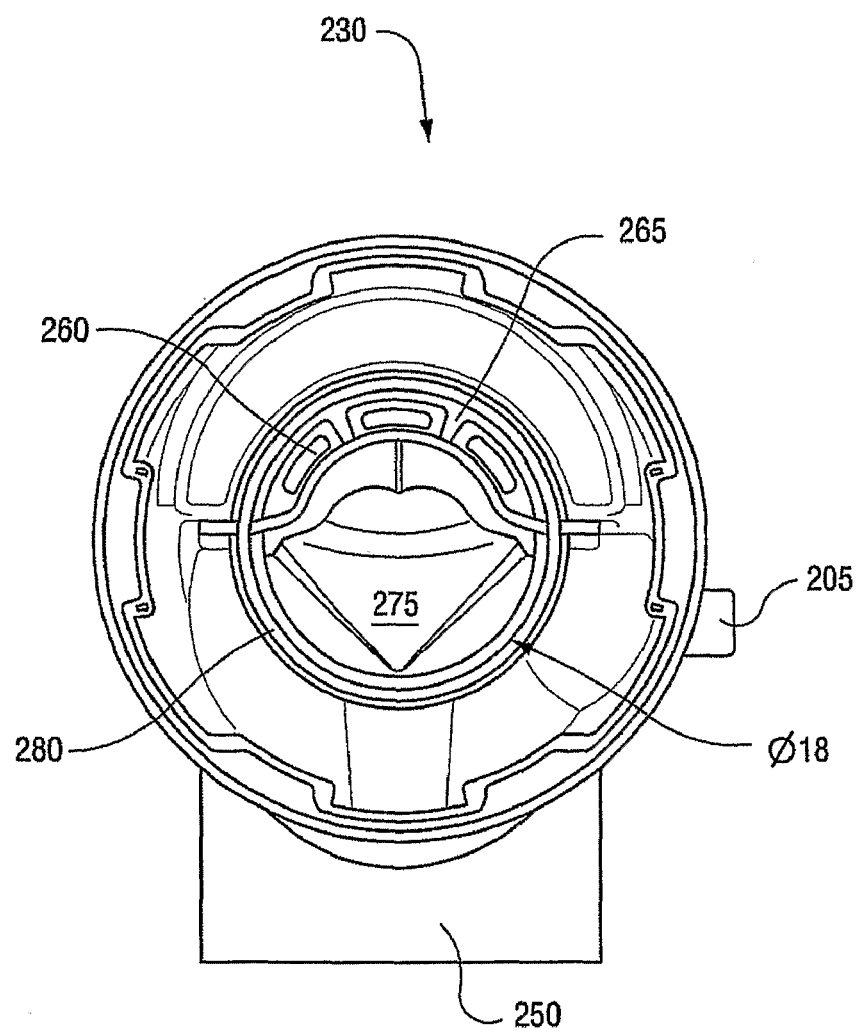
FIG. 11 shows a rear view of the elbow of FIG. 8 and thus shows a view similar to FIG. 7. The dimension shown is in millimeter s.

Another aspect of the invention is the swivel elbow port and its respective port cap. The swivel elbow port 205 is illustrated in FIGS. 8, 9a and 11, and the port cap 115 is illustrated in FIGS. 5-7. By connecting suitable tubing to this port it is possible to inject medical gas (such as $O_2$) into the air circuit, sample gas or take a pressure reading amongst other things. The cap 115 is used to seal the port when the port is not in use. The swivel elbow is removably replaceable. A swivel elbow in accordance with an embodiment of the invention may include none, one or more such ports. For some treatment applications, e.g. home based treatment, access ports may not be required and so a mask may be fitted with an elbow which has no port. For other treatment applications, such as in a hospital, ports may be desired and thus an elbow with a suitable number of ports may be fitted. A problem with some prior art masks which included ports is that the caps kept falling off in use. While this may be tolerated in treatment situations where ports may occasionally be used, in other treatment situations where ports are not desired, this is a nuisance. This it is possible to overcome this problem by assembling a patient's mask with the appropriate number of ports, which may include no ports. Another advantage of including the ports on the swivel elbow is that any associated tubing is less likely to tangle with an air delivery conduit if the air delivery conduit is moved.

Although the invention has been described with reference to preferred embodiments, it is to be understood that these embodiments are merely illustrative of the application of the principles of the invention. Numerous modifications may be made therein and other arrangements may be devised without departing from the spirit and scope of the invention. For example whilst the invention is particularly useful for use with a swivel elbow, the principles of the invention are applicable to masks with non-swivelling elbows. Furthermore, the principles of the invention which reduce interference between incoming and outgoing air streams are applicable to masks without elbows at all, but simply having inflowing and out flowing airstreams near one another.

The invention claimed is:

1. A vent elbow comprising:
a generally L-shaped main body having a frame engaging portion and a base portion;
a conduit pathway to deliver an incoming gas flow stream from the base portion towards the frame engaging portion;
a vent pathway to allow an outgoing gas flow stream to flow from the frame engaging portion towards a vent formed in the main body, the vent pathway being part annular; and
a cylindrical portion extending from the frame engaging portion; and
a baffle provided to the main body to separate and at least partly define the conduit pathway and the vent pathway, wherein the baffle includes a lip portion extending beyond the cylindrical portion, the lip portion having a first surface facing towards an axis of the cylindrical portion and a second surface facing away from the axis of the cylindrical portion, wherein at least a portion of the baffle is part cylindrical and has an axis that is generally concentric with the axis of the cylindrical portion, and the first surface of the lip portion, in cross-section, includes a curved portion that curves away from or towards the axis of the cylindrical portion in a direction along the axis of the cylindrical portion.

2. The vent elbow as claimed in claim 1, wherein the baffle includes ends that connect to the cylindrical portion.

3. The vent elbow as claimed in claim 2, wherein the ends of the baffle subtend at an angle of up to 180 degrees with respect to the axis of the baffle.

4. The vent elbow as claimed in claim 1, wherein the ends of the baffle subtend at an angle of up to 180 degrees with respect to the axis of the baffle.

5. The vent elbow as claimed in claim 4, further comprising at least one spacer that spaces the baffle from the cylindrical portion.

6. The vent elbow as claimed in claim 5, wherein the at least one spacer includes a first pair of spacers that connect ends of the baffle to the cylindrical portion, wherein the spacers are angled relative to the ends of the baffle.

7. The vent elbow as claimed in claim 6, wherein the first pair of spacers define ends of the part annular vent pathway.

8. The vent elbow as claimed in claim 6, wherein the at least one spacer includes a second pair of spacers that connect the baffle to the cylindrical portion along interior portions of the part annular vent pathway.

9. The vent elbow as claimed in claim 6, wherein the first pair of spacers extend in a radial sense between the cylindrical portion and ends of the baffle.

10. The vent elbow as claimed in claim 6, wherein the at least one spacer extends generally perpendicular to the cylindrical portion.

11. The vent elbow as claimed in claim 1, wherein a portion of the conduit pathway and together with the baffle define a generally circular cross section.

12. The vent elbow as claimed in claim 1, wherein the vent pathway includes an inlet positioned adjacent the frame engaging portion and a vent outlet, and wherein the inlet is larger in cross section than the outlet in cross section.

13. The vent elbow as claimed in claim 1, wherein the vent pathway has a first portion having an approximately constant cross section, a second portion having an approximately constant cross section, and a transition region that tapers down from the first portion to the second portion.

14. The vent elbow as claimed in claim 13, wherein the first portion spans about ⅔ of a length of the vent pathway.

15. The vent elbow as claimed in claim 1, wherein the lip portion is structured to extend into a breathing cavity of the mask frame in use to a predetermined depth.

16. The vent elbow as claimed in claim 15, wherein the predetermined depth is at least 1.5 mm.

17. The vent elbow as claimed in claim 15, wherein the predetermined depth is about 1.8 mm.

18. The vent elbow as claimed in claim 15, wherein the predetermined depth is between about 1.5 mm and about 2.5 mm.

19. The vent elbow as claimed in claim 15, wherein the curved portion is curved to help reduce interference between the incoming and outgoing gas streams.

20. The vent elbow as claimed in claim 19, wherein the curved portion is oriented to direct the incoming gas stream away from the outgoing gas stream and the vent.

21. The vent elbow as claimed in claim 19, wherein the curved portion is oriented to smoothly guide the outgoing gas stream towards the vent.

22. The vent elbow as claimed in claim 1, wherein the frame engaging portion includes a series of slots structured to engage with a mask frame in use.

23. The vent elbow as claimed in claim 1, wherein the base portion includes a generally cylindrical section structured to be coupled with an air delivery conduit.

24. The vent elbow as claimed in claim 1, further comprising a port provided to the main body, and a port cap to selectively close or allow access to the port.

25. The vent elbow as claimed in claim 1, wherein the first surface includes an upwardly curved convex portion that curves away from the axis of the cylindrical portion.

26. The vent elbow as claimed in claim 25, wherein the second surface includes an upwardly curved concave portion that curves away from the axis of the cylindrical portion.

27. The vent elbow as claimed in claim 1, wherein the first surface includes a downwardly curved concave portion that curves towards the axis of the cylindrical portion.

28. The vent elbow as claimed in claim 27, wherein the second surface includes an downwardly curved convex portion that curves towards the axis of the cylindrical portion.

29. The vent elbow as claimed in claim 1, wherein the first surface includes a downwardly curved concave portion that curves towards the axis of the cylindrical portion and the second surface includes an upwardly curved concave portion that curves away from the axis of the cylindrical portion.

30. The vent elbow as claimed in claim 29, wherein the second surface includes an downwardly curved convex portion that curves towards the axis of the cylindrical portion.

31. The vent elbow as claimed in claim 1, wherein the first surface includes a downwardly curved concave portion that curves towards the axis of the cylindrical portion, a tip portion that extends substantially parallel to the axis of the cylindrical portion, and a downwardly oriented convex portion disposed between the concave portion and the tip portion.

32. The vent elbow as claimed in claim 31, wherein the tip portion is at an end of the lip portion.

33. A vent elbow comprising:
a generally L-shaped main body having a frame engaging portion and a base portion;
a conduit pathway to deliver an incoming gas flow stream from the base portion towards the frame engaging portion;
a vent pathway to allow an outgoing gas flow stream to flow from the frame engaging portion towards a vent formed in the main body;
a cylindrical portion extending from the frame engaging portion; and
a baffle provided to the main body to separate and at least partly define the conduit pathway and the vent pathway, wherein the baffle includes a lip portion extending beyond the cylindrical portion and structured to extend into a breathing cavity of the mask frame in use to a predetermined depth, the lip portion having a first surface facing towards an axis of the cylindrical portion and a second surface facing away from the axis of the cylindrical portion, and wherein the first surface of the lip portion, in cross-section, includes a curved portion that curves away from or towards the axis of the cylindrical portion in a direction along the axis of the cylindrical portion.

34. The vent elbow as claimed in claim 33, wherein the first surface includes an upwardly curved convex portion that curves away from the axis of the cylindrical portion.

35. The vent elbow as claimed in claim 34, wherein the second surface includes an upwardly curved concave portion that curves away from the axis of the cylindrical portion.

36. The vent elbow as claimed in claim 33, wherein the first surface includes a downwardly curved concave portion that curves towards the axis of the cylindrical portion.

37. The vent elbow as claimed in claim 36, wherein the second surface includes an downwardly curved convex portion that curves towards the axis of the cylindrical portion.

38. The vent elbow as claimed in claim 36, wherein the second surface includes an upwardly curved concave portion that curves away from the axis of the cylindrical portion and a downwardly curved convex portion that curves away from the axis of the cylindrical portion.

39. The vent elbow as claimed in claim 33, wherein the first surface includes a downwardly curved concave portion that curves towards the axis of the cylindrical portion and a tip portion that extends substantially parallel to the axis of the cylindrical portion, and a downwardly oriented convex portion disposed between the concave portion and the tip portion.

40. The vent elbow as claimed in claim 39, wherein the tip portion is at an end of the lip portion.

41. The vent elbow as claimed in claim 39, wherein the second surface includes a downwardly curved portion that extends towards the axis of the cylindrical portion, and a tip portion.

42. A mask assembly comprising:
a mask frame; and
a vent elbow according to claim 1 provided to the mask frame.

43. A mask assembly comprising:
a mask frame; and
a vent elbow according to claim 33 provided to the mask frame.

44. A swivel elbow, comprising:
a frame engaging portion adapted to engage a mask frame in use;
separate conduit and vent airflow pathways for conducting respective gas flow streams in use;
a cylindrical portion extending from the frame engaging portion;

baffle structure that at least partially separates the conduit and vent airflow pathways, the baffle structure including a lip portion extending beyond the cylindrical portion, the lip portion having a first surface facing towards an axis of the cylindrical portion and a second surface facing away from an axis of the cylindrical portion, and wherein the first surface, in side cross-section, includes a curved portion that curves away from or towards the axis of the cylindrical portion.

45. The swivel elbow of claim 44, wherein the first surface includes an upwardly curved portion at a tip of the lip portion that curves away from the axis of the cylindrical portion.

46. The swivel elbow of claim 44, wherein the second surface includes an upwardly curved portion that curves away from the axis of the cylindrical portion.

47. The swivel elbow of claim 44, wherein the first surface includes a downwardly curved portion that curves towards the axis of the cylindrical portion.

48. The swivel elbow of claim 44, wherein the second surface includes a downwardly curved portion that curves towards the axis of the cylindrical portion.

49. The swivel elbow of claim 44, wherein the second surface includes an upwardly curved portion that curves away from the axis of the cylindrical portion and a downwardly curved portion that curves towards the axis of the cylindrical portion.

50. The swivel elbow of claim 44, wherein the first surface includes a downwardly curved portion that curves towards the axis of the cylindrical portion and a tip portion that extends substantially parallel to the axis of the cylindrical portion.

51. The swivel elbow of claim 50, wherein the tip portion is positioned adjacent an end of the lip portion.

52. The swivel elbow of claim 50, wherein the second surface includes a downwardly curved portion that curves towards the axis of the cylindrical portion, and a tip portion that extends substantially parallel to the axis of the cylindrical portion.

53. A mask assembly comprising:
a mask frame; and
a swivel elbow according to claim 44 provided to the mask frame.

* * * * *